(12) United States Patent
Weinberg

(10) Patent No.: US 7,123,967 B2
(45) Date of Patent: Oct. 17, 2006

(54) IMPLANTABLE NEURAL STIMULATION DEVICE PROVIDING ACTIVITY, REST, AND LONG TERM CLOSED-LOOP PERIPHERAL VASCULAR DISEASE THERAPY AND METHOD

(75) Inventor: Lisa P. Weinberg, Moorpark, CA (US)

(73) Assignee: Pacesetter, Inc., Sylmar, CA (US)

( * ) Notice: Subject to any disclaimer, the term of this patent is extended or adjusted under 35 U.S.C. 154(b) by 733 days.

(21) Appl. No.: 10/144,911

(22) Filed: May 13, 2002

(65) Prior Publication Data

US 2003/0212445 A1 Nov. 13, 2003

(51) Int. Cl.
*A61N 1/08* (2006.01)
(52) U.S. Cl. .............................. 607/48; 607/46; 607/19
(58) Field of Classification Search .................... 607/9, 607/62, 116–118, 2, 44–46, 48, 18
See application file for complete search history.

(56) References Cited

U.S. PATENT DOCUMENTS

| | | | | |
|---|---|---|---|---|
| 4,549,556 A * | 10/1985 | Tarjan et al. | ................ | 607/117 |
| 5,031,618 A | 7/1991 | Mullett | ........................ | 128/421 |
| 5,203,326 A * | 4/1993 | Collins | ........................... | 607/4 |
| 5,476,483 A | 12/1995 | Bornzin et al. | ................ | 607/17 |
| 5,514,162 A | 5/1996 | Bornzin et al. | ................ | 607/19 |
| 5,702,429 A * | 12/1997 | King | ............................ | 607/46 |
| 5,707,400 A * | 1/1998 | Terry et al. | .................... | 607/44 |
| 5,749,900 A | 5/1998 | Schroeppel et al. | ........... | 607/4 |
| 6,035,233 A | 3/2000 | Schroeppel et al. | ......... | 600/515 |
| 6,058,331 A | 5/2000 | King | ............................ | 607/62 |
| 6,066,163 A | 5/2000 | John | ........................... | 607/45 |
| 6,134,470 A | 10/2000 | Hartlaub | ....................... | 607/14 |
| 6,144,878 A | 11/2000 | Schroeppel et al. | ......... | 600/515 |
| 6,366,813 B1 * | 4/2002 | DiLorenzo | .................... | 607/45 |
| 6,377,851 B1 * | 4/2002 | Shieh et al. | ................... | 607/9 |

FOREIGN PATENT DOCUMENTS

EP 0944411 B1 4/2001

* cited by examiner

*Primary Examiner*—Robert E. Pezzuto
*Assistant Examiner*—Tammie K Heller

(57) ABSTRACT

An implantable neural stimulation device and method treats peripheral vascular disease of a patient. The device includes a pulse generator that provides stimulation pulses and an implantable lead that applies the stimulation pulses to neural tissue. An activity sensor senses activity level of the patient and a processor, responsive to the activity sensor, controls the provision of the stimulation pulses by the pulse generator. The processor causes the pulse generator to provide stimulation therapy any time the patient is active or when the patient is at rest. The processor further provides long term activity monitoring and closed loop control of neural tissue stimulation levels to adapt the stimulation therapy to changes in the patient's condition.

20 Claims, 4 Drawing Sheets

IMPLANTABLE NEURAL STIMULATION DEVICE PROVIDING ACTIVITY, REST, AND LONG TERM CLOSED-LOOP PERIPHERAL VASCULAR DISEASE THERAPY AND METHOD

FIELD OF THE INVENTION

The present invention generally relates to an implantable stimulation device for treating peripheral vascular disease. The present invention more particularly relates to such a device which provides stimulation therapy when the patient is at rest and is active and which automatically adjusts the degree of stimulation over time in a closed-loop manner.

BACKGROUND

Neural stimulation has been used to treat Peripheral Vascular Disease (PVD). It has been shown to restore tissue health by improving blood flow and reducing ischemia pain in peripheral limbs.

U.S. Pat. No. 6,058,331, incorporated herein by reference, describes a system including an implantable stimulation device for stimulating the spinal cord or a peripheral nerve. The system further includes an external sensor or limb sensor and an ischemia sensor that causes the stimulation to be delivered if the patient is experiencing an episode of ischemia.

Unfortunately, U.S. Pat. No. 6,058,331 and the prior art fail to provide relief in other important instances. These instances include any time the patient is active, any time the patient is at rest, or long term adjustment in the degree of stimulation based upon progression or regression of the patient's condition.

During physical exercise, and for those suffering from PVD, the blood in the peripheral limbs may be shunted. Instead, the blood is delivered to the actual large muscles performing the exercise. This results in claudication pain during exercise. Hence, it would be most beneficial to be able to provide stimulation whenever the patient is active.

With respect to pain when the patient is at rest, and particularly for end stage PVD, ischemia pain can become worse since gravity can no longer assist in promoting blood flow to the lower limbs. Hence, this calls for the ability to detect when the patient is at rest and provide stimulation at those times. This should significantly help any time the patient is lying down and resting for some length of time, such as when the patient is in the sleep state.

Lastly, the degree of stimulation should be controllable over long periods of time in keeping with the progression and regression of the patient's condition. This would require long term closed-loop evaluation and control so that if the patient's condition becomes worse, the degree of stimulation, whether the patient is active or at rest, is increased. Conversely, if the patient's condition improves over time, the degree of stimulation should decrease.

Activity would be a good measure of the progression or regression of PVD. As the condition becomes worse and the patient experiences more claudication and rest pain, the patient will become less active. Conversely, if the patient's PVD improves, the patient will become more active.

The present invention addresses these needs. It provides an implantable stimulation device capable of stimulating neural tissue whenever the patient is active or whenever the patient is at rest. It further provides long term closed-loop control of stimulation degree to fit the progression or regression of the PVD and hence the needs of the patient.

SUMMARY

The present invention provides an implantable neural stimulation device for treating peripheral vascular disease of a patient. The device includes a pulse generator that provides stimulation pulses, an implantable lead that applies the stimulation pulses to neural tissue, and an activity sensor that senses activity level of the patient. A processor, responsive to the activity sensor, controls the provision of the stimulation pulses by the pulse generator. The device includes an enclosure and the pulse generator, activity sensor and processor are all preferably within the device enclosure.

The processor preferably enables the pulse generator to provide the stimulation pulses when the patient is active. The processor first preferably determines a degree of stimulation responsive to the sensed activity level prior to enabling the pulse generator. The processor increases the degree of stimulation responsive to an increased level of activity of the patient. The stimulation pulses have a rate, duration and amplitude. The processor controls the degree of stimulation by varying at least one of rate, duration, and amplitude of the stimulation pulses.

The activity sensor may alternatively or in addition sense an activity level of the patient corresponding to an at rest condition of the patient. The processor controls the pulse generator to provide at rest stimulation pulses corresponding to the at rest condition.

The activity sensor preferably senses activity variance to sense the at rest condition. The processor terminates the provision of the at rest stimulation pulses when the patient is no longer at rest.

The activity sensor may further sense activity level of the patient over an extended long term time period to provide an indication of progression and regression of the peripheral vascular disease. The processor then determines a degree of stimulation responsive to the indication provided by the activity sensor of the progression and regression of the peripheral vascular disease to provide long term closed-loop control. Preferably, the indication is a long term activity average.

The present invention further provides an implantable neural stimulation device for treating peripheral vascular disease of a patient. The device includes stimulation means for providing stimulation pulses, lead means for applying the stimulation pulses to neural tissue, and activity sensing means for sensing activity level of the patient. The device further includes control means responsive to the activity sensing means for controlling the provision of the stimulation pulses by the stimulating means in relation to the activity level of the patient.

The present invention still further provides a method, for use in an implantable neural stimulation device for treating peripheral vascular disease of a patient. The method includes the steps of sensing activity level of the patient, and responsive to the sensed activity level, providing stimulation pulses to neural tissue. The stimulation pulses may be provided when the patient is active or when the patient is at rest, or both. Additionally, different stimulation settings may be employed in the active and at rest states.

The sensing step may include sensing activity level of the patient over an extended long term time period to provide an indication of progression and regression of the peripheral vascular disease. The method may include the further step of determining a degree of stimulation responsive to the indication of the progression and regression of the peripheral vascular disease to provide long term, closed-loop control, of the neural tissue stimulation.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
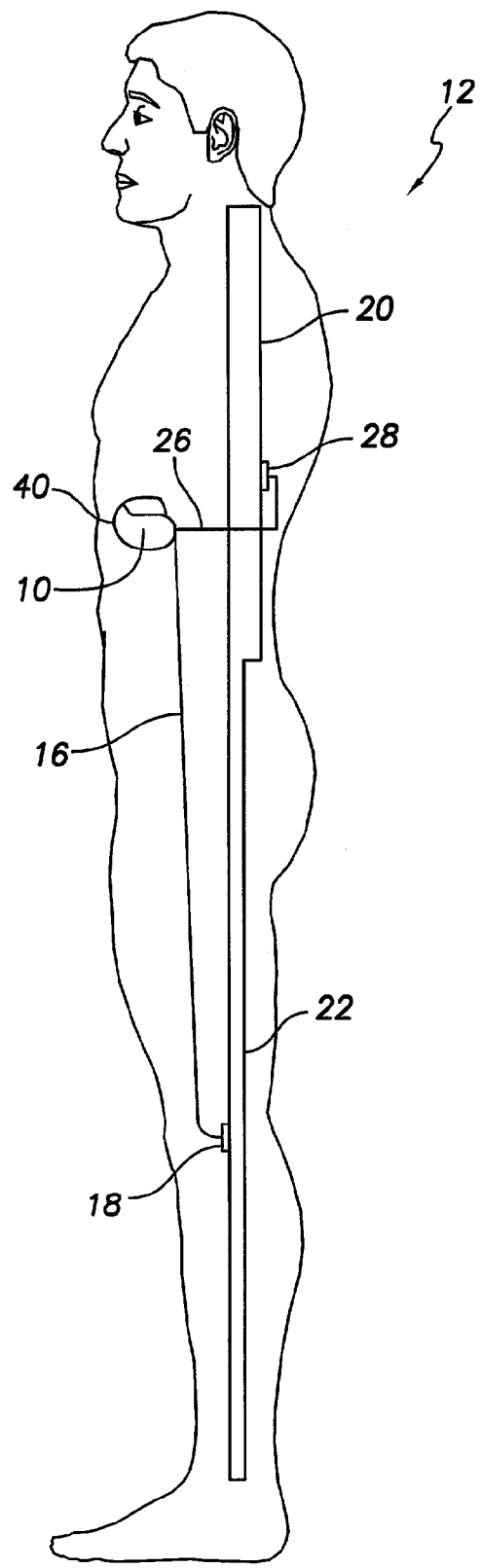
FIG. 1 is a simplified diagram illustrating an implantable stimulation device in electrical communication with at least two leads implanted in a patient for delivering neural tissue stimulation in accordance with an embodiment of the present invention.

As shown in FIG. 1, there is a stimulation device 10 implanted within a patient 12 for providing peripheral vascular disease therapy in accordance with an embodiment of the present invention. The device 10 is implanted within the abdomen of the patient 12. The device 10 includes at least two leads 16 and 26. Leads 16 and 26 are shown for illustrative purposes only and it may be appreciated by those skilled in the art that additional leads may be employed.

The lead 16 couples the device 10 to a peripheral nerve of the patient such as the sciatic nerve 22. To that end, the lead 16 includes an electrode 18 in electrical contact with the sciatic nerve 22.

The lead 26 couples the device 10 to the spinal cord 20 of the patient 12. To that end, the lead 26 includes an electrode 28 in electrical contact with the spinal cord 20. The electrodes 18 and 28 may be epidermal or intrathecal electrodes or may be placed in the neural tissue to be stimulated. Further, the electrodes may be unipolar electrodes wherein the stimulation is provided between the electrode and the enclosure 40 of the device 10 or may be bipolar electrodes as are known in the art.

As will be seen hereinafter, the device 10 includes a physiologic sensor that senses activity of the patient. In accordance with the present invention, whenever activity of the patient is sensed, the device applies stimulation to the neural tissue. Further, the device 10 senses when the patient is at rest. When the patient is at rest, the device then applies at rest stimulation to the neural tissue. The foregoing therapy promotes blood flow to the peripheral extremities of the patient while the patient is active to address claudication pain and while the patient is at rest to address rest pain.

Further, the device 10 in accordance with the present invention provides long term activity monitoring. The long term activity monitoring permits the progression and regression of the peripheral vascular disease to be tracked or monitored. In accordance with this embodiment, the long term monitoring is accomplished by determining a long term activity average. A decrease in long term activity average will indicate that the patient is less active, experiencing pain at lower activity levels and hence is experiencing a progression in the peripheral vascular disease. This will cause the device to in turn increase the degree of neural stimulation. Conversely, an increase in long term activity average will indicate that the patient is more active, experiencing less pain, and hence is experiencing a regression in the peripheral vascular disease. Responsive to such monitoring, the device 10 will decrease the degree of neural stimulation.

Figure 2:
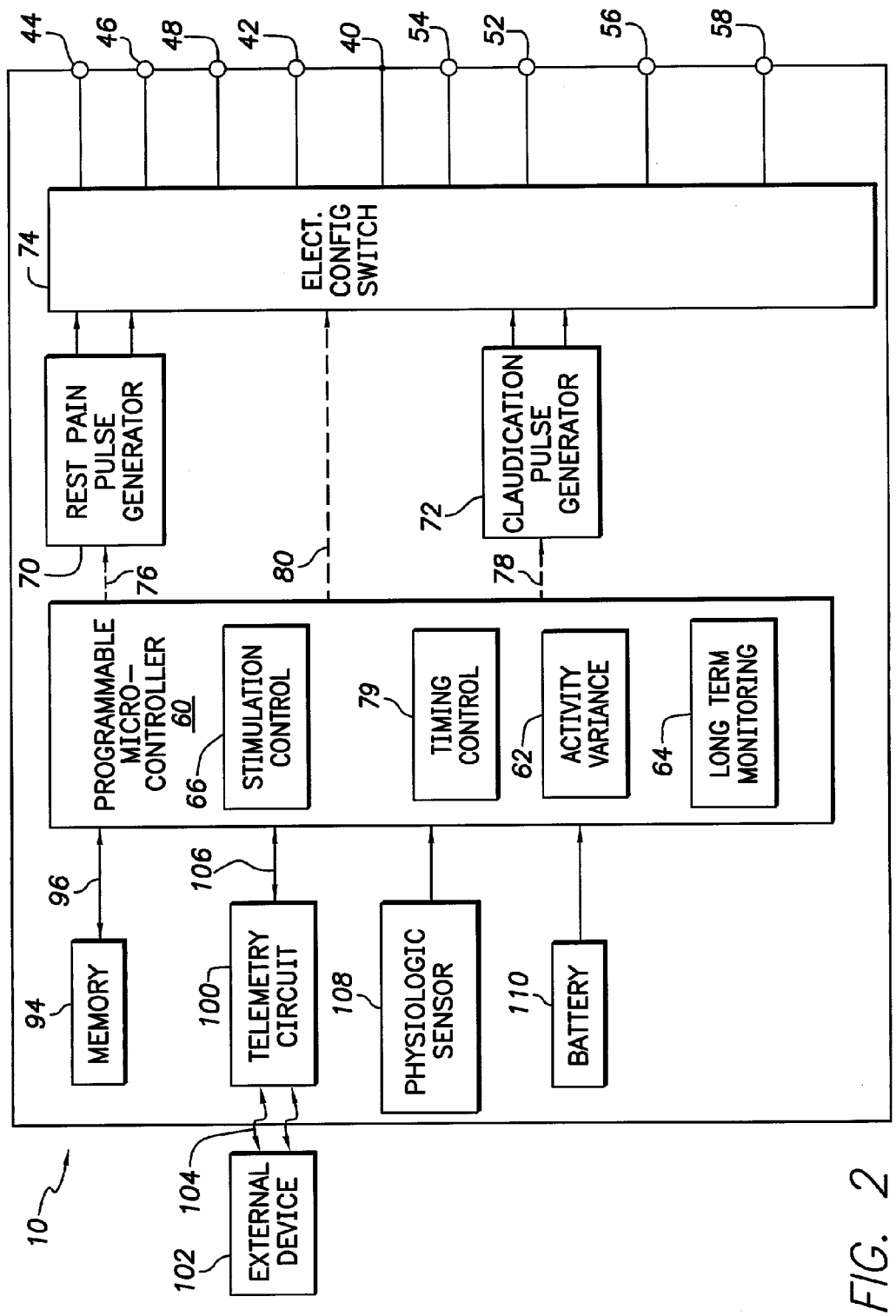
FIG. 2 is a functional block diagram of the implantable stimulation device of FIG. 1.

As illustrated in FIG. 2, a simplified block diagram is shown of the implantable stimulation device 10, which is capable of providing both claudication and at rest stimulation therapy. The device 10 is further capable of providing long term monitoring of the progression and regression of the patient's condition and closed-loop control of stimulation levels or aggressiveness responsive to such monitoring.

The stimulation device 10 includes a housing 40, shown schematically in FIG. 2. The housing 40 is often referred to as the "can", "icase" or "case electrode" and may be programmably selected to act as the return electrode for all "unipolar" neural stimulation. The housing 40 further includes a connector (not shown) having a plurality of terminals, 42, 44, 46, 48, 52, 54, 56, and 58 which may be coupled to respective stimulation electrodes by one or more leads of the type illustrated in FIG. 1. Hence each terminal or terminal pair (for bipolar stimulation) may be dedicated to stimulating neural tissue of a particular extremity such as the left foot, right foot, left leg, or right leg, or the spinal cord itself.

At the core of the stimulation device 10 is a programmable microcontroller 60 which controls the stimulation therapy. As is well known in the art, the microcontroller 60 may include a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, a rest pain pulse generator 70 and a claudication or activity pulse generator 72 generate neural stimulation pulses for delivery to the neural tissue through an electrode configuration switch 74. It is understood that in order to provide stimulation therapy to each of the neural tissue sites, the pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to initiate, terminate, and control the degree of the stimulation pulses. Further to that end, the microcontroller 60 includes timing control circuitry 79 which is used to control the timing of the neural stimulation pulses (e.g., pulse rate, pulse duration or pulse duty cycle.

The switch 74 includes a plurality of switches for connecting the desired neural stimulation electrodes to the appropriate pulse generator, thereby providing complete electrode programmability. Accordingly, the switch 74, in response to a control signal 80 from the microcontroller 60, determines the polarity of the stimulation pulses (e.g., unipolar, bipolar, etc.) by selectively closing the appropriate combination of switches (not shown) as is known in the art.

The microcontroller 60 is further coupled to a memory 94 by a suitable data/address bus 96. The memory stores suitable data and operating instructions to support the microcontroller 60. The memory may also store physician selectable parameters to customize the operation of the stimulation device 10 to suit the needs of a particular patient.

Advantageously, the physician selectable parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows status information relating to the operation of the device 10 (as contained in the microcontroller 60 or memory 94) to be sent to the external device 102 through an established communication link 104.

To sense activity of the patient, the stimulation device 10 includes a physiologic sensor 108. While it is preferred that the sensor 108 be included within the housing 40 of the stimulation device 10, it is to be understood that the physiologic sensor 108 may also be external to the stimulation device 10, yet still be implanted within or carried by the patient. A common type of physiologic sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient.

In accordance with the present invention, the physiologic sensor 108 is used to generate raw activity signals which are used to derive activity measurements and to determine the activity state of the patient. One such activity measurement is activity variance. To that end, the device includes an activity variance circuit 62 which determines activity variance from the raw activity signals provided by the sensor 108. The activity variance is used to determine if the patient is at rest. For a complete description of a manner in which the activity variance may be determined, reference may be made to U.S. Pat. No. 5,476,483 (Bornzin et al.), issued Dec. 19, 1995 or U.S. Pat. No. 5,514,162 (Bornzin et al.) issued May 7, 1996 which patents are hereby incorporated herein by reference.

The stimulation device additionally includes a long term monitoring circuit 64. The long term monitoring circuit determines a long term activity average from the raw activity signals. This enables the patient's condition to be tracked or monitored over time for a progression or regression in the patient's condition. A system and method for monitoring progression of cardiac disease state using physiologic sensors is disclosed for example in copending U.S. patent application Ser. No. 09/746,235, filed Dec. 21, 2000 for SYSTEM AND METHOD FOR MONITORING PROGRESSION OF CARDIAC DISEASE STATE USING PHYSIOLOGIC SENSORS which is incorporated herein by reference.

The long term activity average is utilized by a stimulation control 66. The stimulation control 66 adjusts the degree of stimulation responsive to the long term activity average and hence the progression or regression in the patient's condition. If the stimulation controls see a decrease in the long term activity average, it will increase the degree of neural stimulation by increasing stimulation amplitude, pulse frequency, and/or pulse duration.

The stimulation control 66 also determines from the raw activity signals if the patient is active and to what degree. If the short term activity signals indicate that the patient is currently more active, the stimulation control will also increase the degree of stimulation. In this manner, both short term and long term activity levels are accommodated.

The stimulation device additionally includes a battery 110 which provides operating power to all of the circuits shown in FIG. 2. For the stimulation device 10, the battery 110 must be capable of operating at low current drains for long periods of time and be capable of providing sufficient energy to support the neural stimulation. For example, the neural stimulation may have amplitudes of 0.1 to 20 volts, pulse widths varying from 60 to 1000 microseconds, and repetition rates varying from 5 to 185 Hz or more. Those skilled in the art will appreciate that these ranges may vary. The battery 110 must also have a predictable discharge characteristic so that elective replacement time can be detected.

Figure 3:
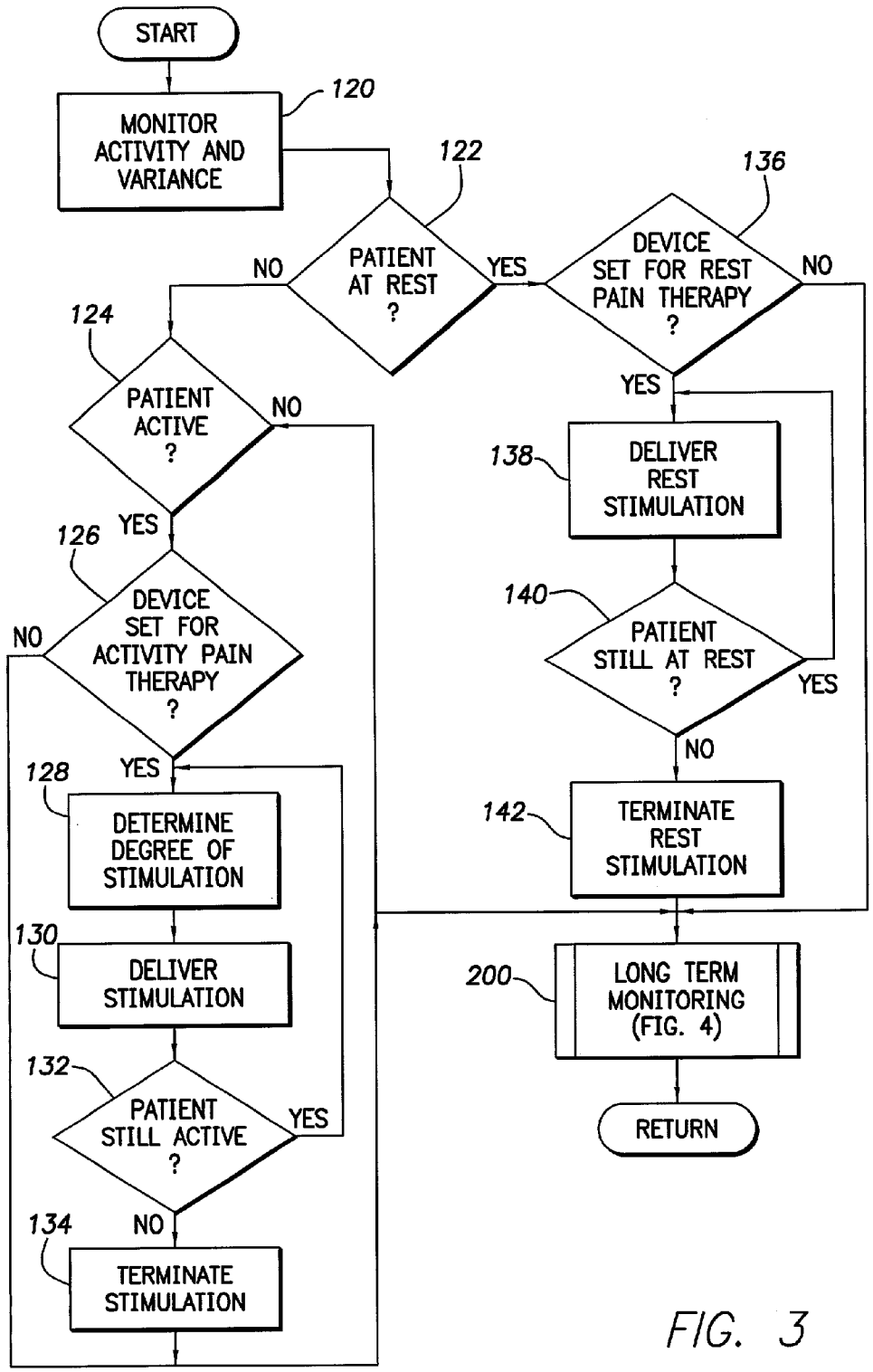
FIG. 3 is a flow chart describing an overview of the operation of one embodiment of the present invention.

In FIG. 3, a flow chart is shown describing an overview of the operation and novel features implemented in one embodiment of the device 10. In this flow chart, and the other flow chart of FIG. 4 described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 3 initiates at an activity block 120. Here, the stimulation control 66 and activity variance circuit 62 utilize the raw activity signals from the physiologic sensor 108 to monitor the activity of the patient. The process then advances to decision block 122 wherein it is determined from the activity variance if the patient is at rest. If the patient is not at rest, the process advances to decision block 124 where it is determined if the patient is currently active. If the activity signals are such that the stimulation control 66 determines that the patient is sufficiently active to provide claudication stimulation, the process advances to decision block 126.

In decision block 126 the microcontroller 60 determines if the device has been set for providing claudication or activity pain therapy. If it has not been so set, the process then immediately advances to a subroutine 200 for long term activity monitoring to be described hereinafter. However, if the device is set for providing activity pain therapy, the process then advances to activity block 128 wherein the stimulation control 66 determines the degree of stimulation required for the level of the patient's activity. Once the degree of stimulation has been determined, the process advances to activity block 130 wherein the claudication pain stimulation is delivered to the neural tissue sites which have been programmed into the device and selected by the configuration switch 74 (FIG. 2). After the stimulation is delivered, the process then advances to decision block 132 wherein it is determined if the patient is still active. If the patient is still active, the process returns to activity block 128 where the degree of stimulation required is once again determined and the stimulation is provided. The foregoing continues until the patient is no longer active as determined by decision block 132. The process then advances to activity block 134 wherein the claudication pain stimulation is terminated and the process then advances to the subroutine 200.

If in decision block 122 it is determined that the patient is at rest, the process then advances to decision block 136 wherein the microcontroller 60 determines if the device has been set for providing rest pain therapy. If the device has not been programmed for providing rest pain therapy, the process then immediately advances to the subroutine 200. However, if the device has been set for providing rest pain therapy, the process then advances to activity block 138 wherein rest stimulation is delivered to the desired neural tissue sites as previously programmed by the physician. After the stimulation is delivered, the process advances to decision block 140 where it is determined if the patient is still at rest. If the patient is still at rest, the process returns to activity block 138 and continues to deliver rest stimulation. When the patient is no longer at rest as determined in decision block 140, the process then advances to activity block 142 for terminating the rest pain therapy. The process then advances to the subroutine 200.

Figure 4:
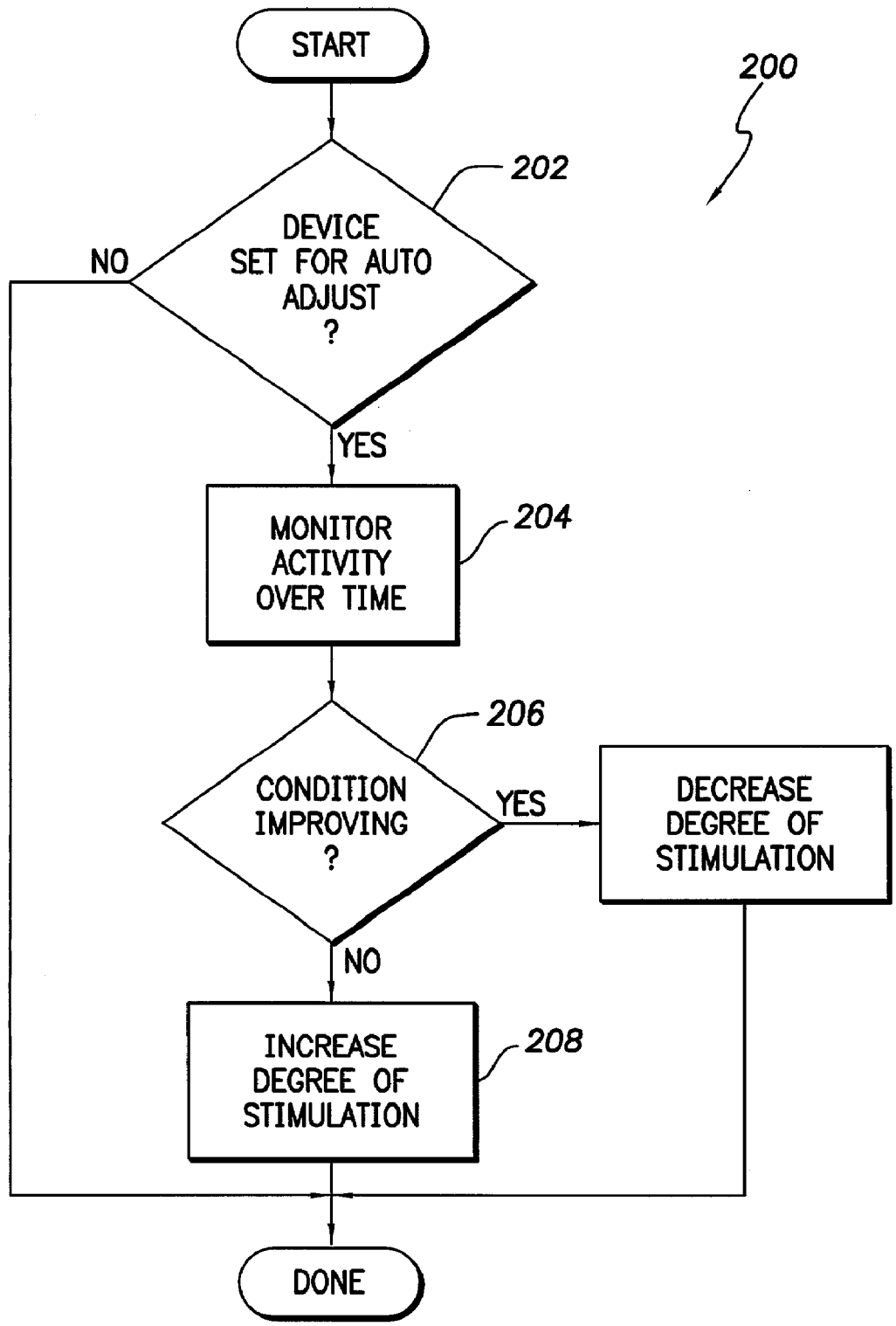
FIG. 4 is a flow chart describing the long term monitoring subroutine of FIG. 3 embodying the present invention.

The subroutine 200 for providing long term monitoring is illustrated in FIG. 4. The subroutine 200 initiates at decision block 202 where it is determined if the device has been programmed to set automatic adjustment of the degree of neural tissue stimulation. If the device has not been so set, the process completes. However, if the device has been set to provide automatic adjustment of the neural tissue stimulation degree, the process then advances to activity block 204 wherein the activity of the patient is monitored over time. In activity block 204, the long term monitoring circuit 64 determines a long term activity average from the raw activity signals provided by the physiologic sensor 108 (FIG. 2).

When the long term activity average has been determined, the process then advances to decision block 206 to determine if the condition of the patient has improved. Here, the microcontroller 60 uses previously generated long term averages and compares them against the current long term average to determine if the patient has become more active or less active. If the patient has become less active, that indicates that there has been a progression in the patient's peripheral vascular disease and requires more aggressive stimulation. However, if the long term activity average indicates that the patient's activity is increasing, less aggressive stimulation will be required.

As a result, and to provide closed loop control, if in decision block 206 it is determined that the patient's condition has not improved, the process then advances to activity block 208 wherein the stimulation control will increase the degree of stimulation provided to the patient. However, if in decision block 206 it is determined that the patient's condition is improving, the stimulation control 66 will decrease the degree of neural tissue stimulation provided to the patient. As a result, long term closed loop control is provided to accommodate the changing needs of the patient.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable neural stimulation device for treating peripheral vascular disease of a patient, the device comprising:
   a pulse generator that is operative to provide stimulation pulses;
   an implantable lead that is configured to apply the stimulation pulses to neural tissue;
   an activity sensor that is operative to sense an activity level of the patient; and
   a processor that is responsive to the activity sensor to control application of the stimulation pulses by the pulse generator;
   wherein the processor enables the pulse generator to provide the stimulation pulses when the patient is active;
   wherein the activity sensor senses activity level of the patient over an extended long term time period to provide an indication of progression and regression of the peripheral vascular disease;
   wherein the processor determines a degree of stimulation responsive to the indication provided by the activity sensor of the progression and regression of the peripheral vascular disease; and
   wherein the processor enables the pulse generator to increase the degree of neural stimulation pulses when a long term activity average decreases.

2. The device of claim 1 wherein the processor determines a degree of stimulation responsive to the sensed activity level prior to enabling the pulse generator.

3. The device of claim 2 wherein the processor increases the degree of stimulation responsive to an increased level of activity of the patient.

4. The device of claim 2 wherein the stimulation pulses have a rate, duration and amplitude, and wherein the processor controls the degree of stimulation by varying at least one of rate, duration, and amplitude of the stimulation pulses.

5. The device of claim 1 further comprising a housing and wherein the activity sensor is within the housing.

6. The device of claim 1 wherein the activity sensor senses an activity level of the patient corresponding to an at rest condition of the patient and wherein the processor controls the pulse generator to provide at rest stimulation pulses corresponding to the at rest condition.

7. The device of claim 6 wherein the activity sensor senses activity variance to sense the at rest condition.

8. The device of claim 6 wherein the processor terminates the provision of the at rest stimulation pulses when the patient is no longer at rest.

9. The device of claim 1 wherein the indication is a long term activity average.

10. An implantable neural stimulation device for treating peripheral vascular disease of a patient, the device comprising:
    a pulse generator that is operative to provide stimulation pulses;
    an implantable lead that is configured to apply the stimulation pulses to neural tissue;
    an activity sensor that is operative to sense an activity level of the patient; and
    a processor that is responsive to the activity sensor to control application of the stimulation pulses by the pulse generator;

wherein the processor enables the pulse generator to provide the stimulation pulses when the patient is active;

wherein the activity sensor senses activity level of the patient over an extended long term time period to provide an indication of progression and regression of the peripheral vascular disease;

wherein the processor determines a degree of stimulation responsive to the indication provided by the activity sensor of the progression and regression of the peripheral vascular disease; and wherein the processor enables the pulse generator to decrease the degree of neural stimulation pulses when a long term activity average increases.

11. An implantable neural stimulation device for treating peripheral vascular disease of a patient, the device comprising:

stimulation means for providing stimulation pulses;

lead means for applying the stimulation pulses to neural tissue;

activity sensing means for sensing activity level of the patient; and control means responsive to the activity sensing means for controlling application of the stimulation pulses by the stimulating means in relation to the activity level of the patient;

wherein the control means comprises means for enabling the provision of the stimulation pulses when the patient is active;

wherein the activity sensing means senses activity level of the patient over an extended long term time period to provide an indication of progression and regression of the peripheral vascular disease;

wherein the control means determines a degree of stimulation responsive to the indication provided by the activity sensor of the progression and regression of the peripheral vascular disease; and wherein the control means enables the stimulation means to increase the degree of stimulation pulses when a long term activity average decreases.

12. An implantable neural stimulation device for treating peripheral vascular disease of a patient, the device comprising:

stimulation means for providing stimulation pulses;

lead means for applying the stimulation pulses to neural tissue;

activity sensing means for sensing activity level of the patient; and control means responsive to the activity sensing means for controlling application of the stimulation pulses by the stimulating means in relation to the activity level of the patient;

wherein the control means comprises means for enabling the provision of the stimulation pulses when the patient is active;

wherein the activity sensing means senses activity level of the patient over an extended long term time period to provide an indication of progression and regression of the peripheral vascular disease;

wherein the control means determines a degree of stimulation responsive to the indication provided by the activity sensor of the progression and regression of the peripheral vascular disease; and wherein the control means enables the stimulation means to decrease the degree of stimulation pulses when a long term activity average increases.

13. The device of claim 12 wherein the control means determines a degree of stimulation responsive to the sensed activity level prior to enabling the provision of the stimulation pulses.

14. The device of claim 13 wherein the control means increases the degree of stimulation responsive to an increased level of activity of the patient.

15. The device of claim 13 wherein the stimulation pulses have a rate, duration and amplitude, and wherein the control means controls the degree of stimulation by varying at least one of rate, duration, and amplitude of the stimulation pulses.

16. The device of claim 12 further comprising an enclosure means for enclosing the activity sensing means, the stimulation means and the control means.

17. The device of claim 12 wherein the activity sensing means senses an activity level of the patient corresponding to an at rest condition of the patient and wherein the control means controls the stimulation means to provide at rest stimulation pulses corresponding to the at rest condition.

18. The device of claim 17 wherein the activity sensing means senses activity variance to sense the at rest condition.

19. The device of claim 17 wherein the control means terminates the provision of the at rest stimulation pulses when the patient is no longer at rest.

20. The device of claim 12 wherein the indication is a long term activity average.

* * * * *